(12) United States Patent
Hunter et al.

(10) Patent No.: US 11,795,458 B2
(45) Date of Patent: Oct. 24, 2023

(54) ANTISENSE OLIGONUCLEOTIDE AND DOUBLE STRANDED RNAS FOR CONTROL OF HEMIPTERAN AND LEPIDOPTERAN PESTS

(71) Applicant: The United States of America, as represented by the Secretary of Agriculture, Washington, DC (US)

(72) Inventors: Wayne B Hunter, Port Saint Lucie, FL (US); Salvador P. Lopez, Vero Beach, FL (US)

(73) Assignee: The United States of America, as represented by The Secretary of Agriculture, Washington, DC (US)

(*) Notice: Subject to any disclaimer, the term of this patent is extended or adjusted under 35 U.S.C. 154(b) by 0 days.

(21) Appl. No.: 17/554,026

(22) Filed: Dec. 17, 2021

(65) Prior Publication Data

US 2022/0195435 A1    Jun. 23, 2022

Related U.S. Application Data

(60) Provisional application No. 63/126,746, filed on Dec. 17, 2020.

(51) Int. Cl.
  *C12N 15/113*    (2010.01)
  *A01N 63/60*     (2020.01)
  *A01P 7/04*      (2006.01)

(52) U.S. Cl.
  CPC .......... *C12N 15/113* (2013.01); *A01N 63/60* (2020.01); *A01P 7/04* (2021.08); *C12N 2310/11* (2013.01); *C12N 2310/321* (2013.01); *C12N 2310/322* (2013.01)

(58) Field of Classification Search
  CPC .............. C12N 15/113; C12N 2310/11; C12N 2310/321; C12N 2310/322; C12N 2310/14; C12N 2310/315; C12N 2310/344; C12N 2310/345; C12N 2310/346; A01N 63/60; A01P 7/04
  See application file for complete search history.

(56) References Cited

U.S. PATENT DOCUMENTS

| | | | |
|---|---|---|---|
| 10,246,710 B2 | 4/2019 | Ghosh et al. | |
| 10,450,583 B2 | 10/2019 | Tsutsui et al. | |
| 2016/0208252 A1* | 7/2016 | Siegfried | ........... C12N 15/8286 |

OTHER PUBLICATIONS

Zhang X, Zheng Y, Jagadeeswaran G, Ren R, Sunkar R, Jiang H. Identification and developmental profiling of conserved and novel microRNAs in Manduca sexta. Insect Biochem Mol Biol. Jun. 2012;42(6):381-95. doi: 10.1016/j.ibmb.2012.01.006. Epub Mar. 1, 2012. PMID: 22406339; PMCID: PMC3340478. (Year: 2012).*

(Continued)

*Primary Examiner* — Ram R Shukla
*Assistant Examiner* — Keyur A Vyas
(74) *Attorney, Agent, or Firm* — John D. Fado; Mark D. McNemar

(57) ABSTRACT

The present disclosure provides oligonucleotides and double-stranded RNAs (dsRNAs) targeting Hemipteran and Lepidopteran insect pests. Bantam-sequence targets are detailed and shown to be effective targets for RNAi induction utilizing multiple dsRNAs, antisense oligonucleotides, and modified dsRNAs (e.g., 2'-O-methylated and dsRNAs containing non-canonical nucleosides).

18 Claims, 9 Drawing Sheets
(9 of 9 Drawing Sheet(s) Filed in Color)
Specification includes a Sequence Listing.

(56) References Cited

OTHER PUBLICATIONS

Jung, J.K. et al. Identification of microRNAs and their target transcripts in the migratory locust adult brain revealed their roles in the epigenetic regulation of polyphenisms. J. of Asia-Pacific Entomology, 2017, 20, 1396-1401. doi.org/10.1016/j.aspen.2017.10.007 (Year: 2017).*
Sharfstein, S. Non-protein biologic therapeutics. Current Op. in Biotech. 2018, 53, 65-75. doi.org/10.1016/j.copbio.2017.12.014 (Year: 2018).*
Christiaens, O. et al. Double-Stranded RNA technology to control insect pests: current status and challenges. Frontiers in Plant Science, Apr. 11, 2020 (1-10). doi.org/10.3389/fpls.2020.00451 (Year: 2020).*
Mone et al., Characterization and expression profiling of microRNAs in response to plant feeding in two host-plant strains of the lepidopteran pest Spodoptera frugiperda, 2018, BMC Genomics, 19, 804, p. 1-15 (Year: 2018).*
NCBI, GenBank Accession No. NR_107264.1, 'Bombyx mori microRNA bantam (bantam), microRNA', Dec. 11, 2014. The Whole Document.
NCBI, GenBank Accession No. XR_002697090.1, 'PREDICTED: Spodoptera litura uncharacterized LOC 111358833 (LOC111358833), ncRNA', Nov. 4, 2017. The Whole Document.
NCBI, GenBank Accession No. XR_002429808.1, 'Predicted: Helicoverpa armigera uncharacterized LOC110380339 (LOC110380339), ncRNA', Jun. 1, 2017. The Whole Document.
International Search Report.

* cited by examiner

A

B

A B

SEQUENCE LISTING

```
<160> NUMBER OF SEQ ID NOS: 8

<210> SEQ ID NO 1
<211> LENGTH: 22
<212> TYPE: RNA
<213> ORGANISM: Artificial Sequence
<220> FEATURE:
<223> OTHER INFORMATION: Chemically Synthesized

<400> SEQUENCE: 1
aaucagcuuu cacaaugauc uc                                              22

<210> SEQ ID NO 2
<211> LENGTH: 22
<212> TYPE: RNA
<213> ORGANISM: Artificial Sequence
<220> FEATURE:
<223> OTHER INFORMATION: Chemically Synthesized

<400> SEQUENCE: 2
gagaucauug ugaaagcuga uu                                              22

<210> SEQ ID NO 3
<211> LENGTH: 188
<212> TYPE: RNA
<213> ORGANISM: Artificial Sequence
<220> FEATURE:
<223> OTHER INFORMATION: Chemically Synthesized

<400> SEQUENCE: 3
uaauacgacu cacuauaggg agaccgaaau aacgaaacug gcauucacag ugaucugcug     60
acauauuuua cggaaaucau agggacgaaa ucagcuuuca caaugaucuc agaaauccga    120
```

```
aauaacgaaa cuggcauuca cagugaucug cugacauauu uuacgucucc cuauagugag    180
ucguauua                                                              188

<210> SEQ ID NO 4
<211> LENGTH: 93
<212> TYPE: RNA
<213> ORGANISM: Artificial Sequence
<220> FEATURE:
<223> OTHER INFORMATION: Chemically Synthesized

<400> SEQUENCE: 4
ccgaaauaac gaaacuggca uucacaguga ucugcugaca uauuuuacga uuucgagau     60 cauugugaaa gcugauuucg ucccuaugau uuc                                 93

<210> SEQ ID NO 5
<211> LENGTH: 68
<212> TYPE: RNA
<213> ORGANISM: Artificial Sequence
<220> FEATURE:
<223> OTHER INFORMATION: Chemically Synthesized

<400> SEQUENCE: 5
uaaaaggaau uacgaaacug guuucauaa ugauuugaca gauuguucua aauucugaga     60
ucauugug                                                             68

<210> SEQ ID NO 6
<211> LENGTH: 96
<212> TYPE: RNA
<213> ORGANISM: Artificial Sequence
<220> FEATURE:
<223> OTHER INFORMATION: Chemically Synthesized

<400> SEQUENCE: 6
uagaggcgug aagagcacga agaaagaaua aaaggaauua cgaaacuggu uuucauaaug    60
auuugacaga uuguucuaaa uucugagauc auugug                              96

<210> SEQ ID NO 7
<211> LENGTH: 69
<212> TYPE: RNA
<213> ORGANISM: Artificial Sequence
<220> FEATURE:
<223> OTHER INFORMATION: Chemically Synthesized

<400> SEQUENCE: 7
agaaaaggaa uaacgaaacu gguuuucaua augauuugac agauuguuca auauucugag    60
aucauugug                                                            69

<210> SEQ ID NO 8
<211> LENGTH: 23
<212> TYPE: RNA
<213> ORGANISM: Artificial Sequence
<220> FEATURE:
<223> OTHER INFORMATION: Chemically Synthesized

<400> SEQUENCE: 8
uaauacgacu cacuauaggg aga                                            23
```

ANTISENSE OLIGONUCLEOTIDE AND DOUBLE STRANDED RNAS FOR CONTROL OF HEMIPTERAN AND LEPIDOPTERAN PESTS

CROSS-REFERENCE

The present application claims priority to U.S. Provisional Patent Application Ser. No. 63/126,746 filed Dec. 17, 2020, the content of which is expressly incorporated herein by reference.

BACKGROUND OF THE INVENTION

Field of Invention

The present disclosure provides oligonucleotides and double-stranded RNAs (dsRNAs) targeting Hemipteran and Lepidopteran insect pests. Bantam-sequence targets are detailed and shown to be effective targets for RNAi induction utilizing multiple dsRNAs, antisense oligonucleotides, and modified dsRNAs (e.g., 2'-O-methylated and dsRNAs containing non-canonical nucleosides).

Background

Lepidopteran pests that threaten world food security include the Fall armyworm, *Spodoptera frupperda*, and the cutworm, *Spodoptera litura* (Fab.) (Lepidoptera: Noctuidae). These pests attack over 120 plant species including maize, grain crops, soybean, cotton, tobacco, vegetables, fruits, and ornamentals worldwide. Lepidopteran species, in the genus *Spodoptera* include the fall armyworm, and others that are considered the most serious pests of grain crops, and are the limiting factors of food security and production in African countries, Asia, and India, which depend on rice and maize production as the main staple. Hemipteran pests include the majority of insect vectors of plant pathogens that limit food security and production globally. The Hemiptera includes the most important insect vectors of plant pathogens (viruses and bacteria), like *Diaphorina citri* (Asian citrus psyllid) the insect vector for the bacterium Candidatus Liberibacter asiaticus (CLas) that causes huanglongbing (citrus greening disease) in citrus. The psyllid and pathogen cause the most serious threat to citrus production worldwide. CLas bacterial infections result in citrus tree decline, lost yields, and tree death (Kruse et al, Insects, (2019) 10: 300; doi:10.3390/insects10090300). Similarly, leafhoppers transmit the bacterium, Xylella fastidiosa, that causes 'scorch-like' diseases in fruit and nut crops, woody ornamentals, and Pierce's disease of grapevines. The insect and pathogen seriously threaten food security around the globe in many countries and is decimating Olives in Europe and the Middle-East. Currently there are no suitable treatments for either of these bacterial caused diseases nor their insect vectors (Psyllids or Leafhoppers). The indiscriminate and large-scale use of synthetic chemical pesticides to manage such pests has resulted in development of resistance against many synthetic insecticides. Thus, in order to offer growers alternates to harmful insecticides the instant disclosure provides novel biocontrol mechanisms utilizing oligonucleotides and dsRNAs targeting these pests.

SUMMARY OF THE INVENTION

The present disclosure provides, in one embodiment, double-stranded ribonucleic acids (dsRNA) having a first strand with a sequence with at least 95% identity to a portion of at least 19 consecutive nucleotides of any one of SEQ ID NO:1, SEQ ID NO:2, SEQ ID NO:3, SEQ ID NO:4, SEQ ID NO:5, SEQ ID NO: 6; or SEQ ID NO: 7 and a second strand complementary to the first strand. In some embodiments, the first strand has at least 99% or 100% sequence identity to any one of SEQ ID NO:1, SEQ ID NO:2, SEQ ID NO:3, SEQ ID NO:4, SEQ ID NO:5, SEQ ID NO: 6; or SEQ ID NO: 7. In particular embodiments, the first strand has the exact sequence of SEQ ID NO:1, SEQ ID NO:3, or SEQ ID NO:4. In most embodiments, the dsRNAs of the present disclosure are capable of inducing ribonucleic acid interference (RNAi) when ingested by a hemipteran or lepidopteran insect, such as *S. frugiperda* or *D. citri*. In some embodiments, dsRNAs have at least one base modified with a 2'-O-methyl moiety. In some embodiments, dsRNAs described herein, have at least one non-canonical nucleotide, such as 2'-fluorine-dCTP or 2'-fluorine-dUTP. In specific embodiments, dsRNAs described herein have each cytosine replaced with 2'-fluorine-dCTP and each uracil comprises 2'-fluorine-dUTP.

In an additional embodiment, the present disclosure provides DNA molecules having a promoter functional in a host cell and a DNA encoding a dsRNA with a first strand and a second strand, where the first strand has a sense region with at least 95% sequence identity a portion of at least 19 consecutive nucleotides of any one of SEQ ID NO:1, SEQ ID NO:2, SEQ ID NO:3, SEQ ID NO:4, SEQ ID NO:5, SEQ ID NO: 6; or SEQ ID NO: 7 and a second strand complementary to the first strand.

Also provided herein is a method of inducing RNAi in a hemipteran or lepidopteran insect, with the steps of contacting the dsRNAs described above with a hemipteran or lepidopteran insect such that the insect ingests the dsRNA, thereby inducing RNAi in the insect. In particular embodiments, the insect is *S. frugiperda* or *D. citri*. In specific embodiments, the dsRNA has the sequence of SEQ ID NO: 1, SEQ ID NO: 2, SEQ ID NO: 3, SEQ ID NO: 4, SEQ ID NO: 5, SEQ ID NO: 6, and SEQ ID NO: 7.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

DETAILED DESCRIPTION OF THE INVENTION

Figure 1:
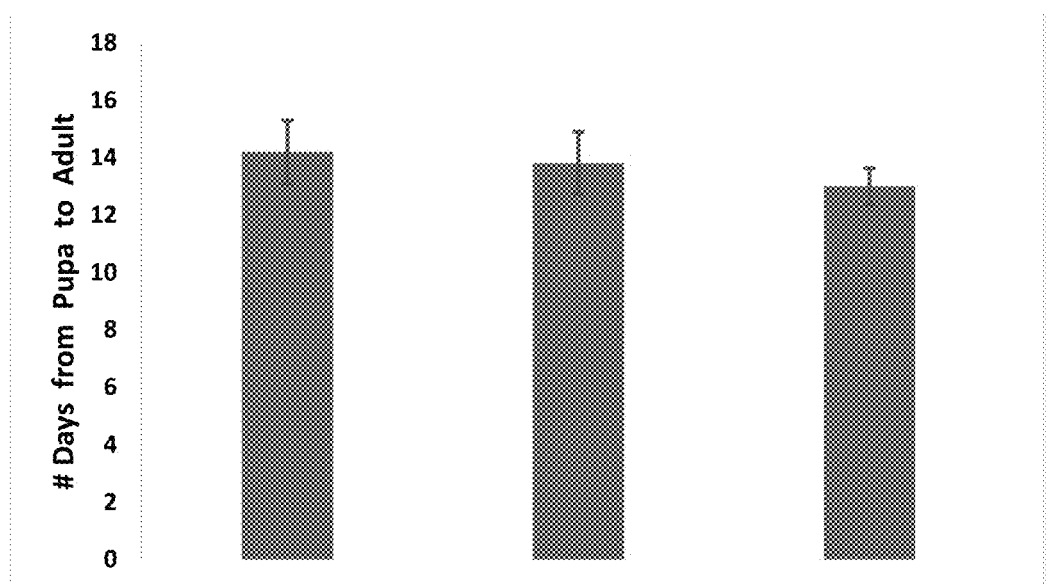
FIG. 1 provides graphic representation of data demonstrating effects on the duration of *Spodoptera* pupation on larvae treated with bantam-antisense oligonucleotide (SEQ ID NO: 1). The first bar represents control larvae, the second bar 2 nmol bantam-ASO, and the third bar 4 nmol bantam-ASO.

Lepidopteran pests that threaten world food security include the armyworm, Spodoptera frugiperda and the cutworm, Spodoptera litura (Fab.) (Lepidoptera: Noctuidae). These pests attack over 120 plant species including maize, grain crops, soybean, cotton, tobacco, vegetables, fruits, and ornamentals worldwide. Hemipteran pests, such as the Asian citrus psyllid (Diaphorina citri), also cause extensive damage and vector plant diseases such as citrus greening, or huanglongbing (HLB). Indiscriminate and large-scale use of synthetic chemical pesticides to manage these pests has resulted in development of resistance against many synthetic insecticides. Biopesticides, like double-stranded RNA (dsRNA), and antisense oligonucleotides (ASO) offer growers safer more species-specific alternates to broad spectrum insecticides. Therefore, we sought to produce and analyze various ASOs and dsRNAs for efficacy in reducing pest survival and development. As disclosed herein, the findings indicate that dsRNAa and ASOs targeting specific genes can be integrated into current pest management programs to increase successful management of these two lepidopteran pests across all agroecosystems.

In insects, miRNAs ("miR") have been shown to regulate a variety of physiological processes throughout insect development, including molting, metamorphosis, oogenesis, embryogenesis, behavior and host-pathogen interactions. The-miR-14 (identified in the psyllid) is a core component pathway important for various developmental processes, regulating fat and sugar metabolism for energy, also functions in the degradation of the larval salivary gland during pupal development by regulating autophagy in salivary gland cells, so may disrupt feeding and pathogen transmission in hemipteran insects like psyllids, leafhoppers, whitefly, if suppressed. The miR-bantam controls growth and proliferation in the posterior signaling center, a stem cell-like niche, by functioning upstream of the insulin signaling pathway, is well documented in flies (Hipfner et al, Genetics, (2002)161:1527-36). We have identified this miRNA in the psyllid Diaphorina citri, leafhopper, whitefly, and the lepidopteran Spodoptera frugiperda as knockdown targets for control of such pests.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing genetically altered strains of *A. pullulans*.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences that are shorter or longer than the reference nucleic acid sequence, have different residues at particular positions, or a combination thereof.

As used in the specification and claims, use of the singular "a", "an", and "the" include plural references unless the context clearly dictates otherwise.

The terms "isolated", "purified", or "biologically pure" as used herein, refer to material that is substantially or essentially free from components that normally accompany the referenced material in its native state.

The terms "about" and "approximately" are defined as plus or minus ten percent of a recited value. For example, about 1.0 g means 0.9 g to 1.1 g and all values within that range, whether specifically stated or not.

"Citrus" as used herein refers to any species of tree producing any variety of citrus fruit, such as oranges, tangerines, clementines, lemons, limes, grapefruit, pummelo, and the like.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C; A< >U) and reading in the 5' to 3' direction, i.e., in opposite direction of the represented nucleotide sequence.

As used herein, "dsRNA" refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single-stranded RNA, but contains at least 19 nucleotides double-stranded RNA. In one embodiment of the invention, a dsRNA comprises a hairpin RNA which contains a loop or spacer sequence between the sense and antisense sequences of the gene targeted, preferably such hairpin RNA spacer region contains an intron, particularly the rolA gene intron (Pandolfini et al., 2003, BioMedCentral (BMC) Biotechnology 3:7 (www.biomedcentral.com/1472-6750/3/7)), the dual orientation introns from pHellsgate 11 or 12 (see, WO 02/059294 and SEQ ID NO: 25 and 15 therein) or the pdk intron (*Flaveria trinervia pyruvate* orthophosphate dikinase intron 2; see WO99/53050). Particular dsRNA species can be referred to by their sequence, whether presented as a DNA or RNA sequence.

Included in this definition are "siRNAs" or small interfering (double-stranded) RNA molecules of 16-30 bp, 19-28 bp, or 21-26 bp, e.g., such as the RNA forms that can be created by RNAseIII or dicer activity from longer dsRNA. siRNAs as used herein include any double-stranded RNA of 19 to 26, or 21 to 24 base pairs that can interfere with gene expression when present in a cell wherein such gene is expressed. siRNA can be synthetically made, expressed and secreted directly from a transformed cell or can be generated from a longer dsRNA by enzymatic activity. These siRNAs can be blunt-ended or can have overlapping ends. Also, modified microRNAs comprising a portion of a target gene and its complementary sequence are included herein as dsRNAs.

The term "control", and grammatical variants thereof, is utilized in several contexts herein. Within experiments, a "control" is a means by which experimental variables are tested to eliminate as a cause of observed results. With regards to diseases (e.g., citrus greening), the term "control" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. With regards to organisms (e.g., insects, bacteria, etc.), the term "control" as used herein refers to any means for preventing infection or infestation, reducing the population of already infected areas, or elimination of population(s) whose "control" is desired. Indeed, "controlling" as used herein refers to any indicia of success in prevention, elimination, reduction, repulsion, or amelioration of a target population or a problem caused by the target population (e.g., insect pest, microbe, etc).

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

"Insect" or "insect pest" as used herein means any variety of insects that may cause harm to plants, trees, fruits, or nuts or products produced thereby or therefrom. In exemplary embodiments, such pests include leaf-eating and sap-feeding arthropods, such as the Asian citrus psyllid.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like).

As used herein, "preventing" a disease refers to inhibiting the full development of a disease.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman & Wunsch, J. Mol. Biol., (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

Double-Stranded RNA and RNA Interference

Since its inception, RNAi has proved to be a potent tool to study gene function and regulation. The advent of bioinformatics coupled with next-generation high throughput sequencing unveiled an array of transcriptomic data available for a wide range of species at different stages of development and tissues. To attain an effective RNAi response in the biocontrol of pests, an accurate and precise mode of dsRNA delivery, efficient uptake and dsRNA stability are of utmost consideration.

Preferably, the dsRNAs to be used in this invention target at least one target insect gene and comprise at least 19 consecutive nucleotides occurring in identical sequence or with high sequence identity in the one or more target insects. In preferred embodiments of this invention, such dsRNAs do not silence host genes, or the genes of other non-target animals, such as humans, beneficial insects (e.g., pollinators), pest predators, or wildlife such as reptiles, amphibians, birds, or mammals. Levels of identity between sequences of interest can be analyzed in available databases, e.g., by a BLAST search (see also www.ncbi.nlm.nih.gov/BLAST) or by hybridization with existing DNA libraries of representative non-target organisms.

As used herein, nucleotide sequences of RNA molecules can be identified by reference to DNA nucleotide sequences of the sequence listing. However, the person skilled in the art will understand whether RNA or DNA is meant depending on the context. Furthermore, the nucleotide sequence is identical between the types of polynucleotides except that the T-base is replaced by uracil (U) in RNA molecules.

In some embodiments, the length of the first (e.g., sense) and second (e.g., antisense) nucleotide sequences of the dsRNA molecules of the invention can vary from about 10 nucleotides (nt) up to a length equaling the length in nucleotides of the transcript of the target gene. The first and second sequences can be referred to as first and second strands. Additionally, it is understood that either the first or second sequence can be the sense or antisense strand. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known that also meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of the target gene. However, it is preferred that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is preferred that the antisense nucleotide sequence includes a sequence of 19 or 20, about 19 or about 20 consecutive nucleotides, although longer stretches of consecutive nucleotides such as about 50 nucleotides, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, a dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can base-pair amongst themselves.

The dsRNAs disclosed herein can be stabilized using chemically modified versions, such as by the use of noncanonical nucleotides (e.g., 2'-fluorine-dCTP, 2'-fluorine-dUTP). Additionally, dsRNAs disclosed herein can have one or more individual nucleotides modified by the addition of 2'-O-Methyl. Other modification techniques are known in the art and are contemplated herein.

Specific dsRNAs of the present invention are provided in Table 1.

| Descriptor | Sequence | SEQ ID NO: |
|---|---|---|
| Antisense bantam | AAUCAGCUUUCACAAUGAUCUC | SEQ ID NO: 1 |
| Sense bantam | GAGAUCAUUGUGAAAGCUGAUU | SEQ ID NO: 2 |
| bantam dsRNA | UAAUACGACUCACUAUAGGGAGACCGAAAU AACGAAACUGGCAUUCACAGUGAUCUGCUG ACAUAUUUUACGGAAAUCAUAGGGACGAAA UCAGCUUUCACAAUGAUCUCAGAAAUCCGA AAUAACGAAACUGGCAUUCACAGUGAUCUG CUGACAUAUUUUACGUCUCCCUAUAGUGAG UCGUAUUA | SEQ ID NO: 3 |
| D. citri Bantam anti sense oligo- nucleotide | CCGAAAUAACGAAACUGGCAUUCACAGUGA UCUGCUGACAUAUUUUACGAUUUCUGAGAU CAUUGUGAAAGCUGAUUUCGUCCCUAUGAU UUC | SEQ ID NO: 4 |
| S. frugiperda miR-bantam Precursor dsRNA Unmodified | UAAAAGGAAUUACGAAACUGGUUUUCAUAA UGAUUUGACAGAUUGUUCUAAAUUCUGAGA UCAUUGUG | SEQ ID NO: 5 |
| S. litura Bantam sense dsRNA | UAGAGGCGUGAAGAGCACGAAGAAAGAAUA AAAGGAAUUACGAAACUGGUUUUCAUAAUG AUUUGACAGAUUGUUCUAAAUUCUGAGAUC AUUGUG | SEQ ID NO: 6 |
| H. armigera dsRNA precursor microRNA bantam | AGAAAAGGAAUAACGAAACUGGUUUUCAUA AUGAUUUGACAGAUUGUUCAAUAUUCUGAG AUCAUUGUG | SEQ ID NO: 7 |
| T7 Promoter | UAAUACGACUCACUAUAGGGAGA | SEQ ID NO: 8 | dsRNA Compositions

In particular embodiments, the present invention provides a composition having one or more dsRNAs having the sequence of one or more of SEQ ID NOs. 1-7. Typically, nucleic acids of the present invention are provided to a target recipient (e.g., plant, insect or bacteria) in an amount sufficient to induce RNA silencing, thereby inhibiting production of the polypeptide encoded by one or more of the full-length genes targeted by SEQ ID NOs. 1-7. For example, a dsRNA of the present invention is applied to a plant topically, allowing for uptake of the dsRNA by the plant. The dsRNA can control a pest feeding on the plant, or otherwise contacting the applied dsRNA. Additionally, when a plant pest (e.g., D. citri) is feeding on a treated plant, the insect can ingest a sufficient level of the dsRNA to control or kill bacteria harbored by the insect pest and/or control or kill the insect pest itself.

In addition to a dsRNA of the present invention, compositions of the present invention intended to be applied to a plant can be formulated so as to contain one or more phagostimulants, pesticides, fungicides, or combinations thereof. The composition can be formulated to be coated on a plant, plant part, plant tissue (e.g., root or leaf), or seed. In certain aspects the dsRNA is combined with one or more excipients, buffering agents, carriers, etc. Such components are well known in the art and readily chosen for various applications by one skilled in the art.

Typically, a dsRNA of the present invention is provided to a target insect pest, target plant in need of treatment, or target microbe in an amount sufficient to inhibit production of the polypeptide encoded by one or more of the full-length genes targeted by dsRNAs. For example, when an insect pest is feeding on dsRNA-laden plant material (e.g., leaf), the insect ingests a sufficient level of dsRNA to result in a phenotypic effect on a bacterium harbored in its gut. In some embodiments, a combination of two or more dsRNAs can be combined in a single plant. In embodiments where two or more dsRNAs are combined in a single plant, the dsRNAs can target different genes or different portions of the same gene from the same or different targets. Thus, in one embodiment, a single plant material can be used to deliver multiple, different dsRNAs targeting the production of one or more proteins made by the treated plant, the insect pest, and/or a microbe present in the plant or in the insect. Where two or more dsRNAs are taken up and distributed throughout the plant material, the dsRNAs can be provided to the plant in a single solution, or in multiple, sequentially-applied solutions.

In addition to dsRNA, compositions of the present invention that are intended to be applied to a plant can also comprise one or more chemoattractants, phagostimulants, visual attractants, insecticides, pheromones, fungicides, or combinations thereof. Such additional components are well known in the art and are readily chosen to complement compositions of the present invention, but are not specifically integral to the present invention. These additional components can be formulated to be coated on a plant, plant part, leaf, fruit, vegetable, stem or other plant structure. In certain aspects the additional component(s) are combined with one or more excipients, buffering agents, carriers, etc. that are also well known in the art.

Where additional components are applied in a coating, the coating can be formulated as a spray or dip so that the additional non-dsRNA components remain on the exterior of the plant material. For example, a leaf having a dsRNA distributed through at least part of its vascular system can be coated with a composition comprising one or more chemoattractants, phagostimulants, visual attractants, insecticides, pheromones, fungicides, or combinations thereof. Alternately, the additional component can be mixed with an aqueous solution containing the dsRNA(s) to be taken up and distributed via vascular action of the plant material, or osmosis through the plant material, thus distributing the dsRNA(s) and the additional component(s) throughout at least part of the plant material.

Application to Target Plants

Compositions of the invention disclosed herein can be applied to soil, fruits, vegetables, crops, and any other desired target using any delivery methodology known to those of skill in the art. For example, dsRNA-containing compositions can be applied to the desired locale via methods and forms including, but not limited to, shank injection, sprays, baits, granules, flood/furrow methods, sprinklers, fumigation, root soaking and drip irrigation. In embodiments of the invention where the compositions are sprayed onto a desired locale, the compositions can be delivered as a liquid suspension, emulsion, microemulsion or powder. In other embodiments, granules or microcapsules can be used to deliver the compositions of the invention.

The compositions of the present invention can be applied to plants and/or crops by any convenient method, for example, by using a fixed application system such as a center pivot irrigation system. Preferably, application to fields of plants and/or crops is made by air spraying, i.e., from an airplane or helicopter, or by land spraying. For example, land spraying may be carried out by using a high flotation applicator equipped with a boom, by a back-pack sprayer or by nurse trucks or tanks. One of skill in the art will recognize that these application methodologies are provided by way of example and that any applicable methods known in the art or developed in the future can be utilized.

Having generally described this invention, the same will be better understood by reference to certain specific examples, which are included herein to further illustrate the invention and are not intended to limit the scope of the invention as defined by the claims.

EXAMPLES

Example 1

Antisense Oligonucleotide Design

The specific bantam sequence for *Spodoptera frupperda* was not available in public databases, but was identified by comparative analyses for bantam across multiple insect species (NCBI nr database: specifically: *Bombyx mori* (NR_107264.1), *Spodoptera litura* (XR_002697090.1), *Tribolium castaneum* (NR_036317.1), *Apis mellifera* (NR_031508.1), and *Acyrthosiphon pisum* (NR_040122.1. Multiple sequence alignment analyses identified a 22 bp region of the bantam miRNA that was highly conserved across these species. Three unique constructs were designed specifically to the: 1) ssRNA sense oligo (SEQ ID NO: 2), 2) ssRNA complementary to the antisense oligo (SEQ ID NO: 1), and 3) and 2'O-Me modified ssRNA complementary to the antisense oligo (Table 1). The 2'O-Me modified oligo has the sequence denoted in SEQ ID NO: 1, however it comprises four phosphorothioated bases on the 5' end and three phosphorothioated based on the 3' end, with all other nucleosides having the 2'O-Me modification. Constructs were ordered from Integrated DNA Technologies, Inc. (IDT). In this trial, only the 2'O-Me antisense oligo was evaluated.

dsRNA Design

Sequences for bantam across multiple insect species were acquired from the NCBI database, specifically: *Bombyx mori* (NR_107264.1), *Spodoptera litura* (XR_002697090.1), *Tribolium castaneum* (NR_036317.1), *Apis mellifera* (NR_031508.1), *Acyrthosiphon pisum* (NR_040122.1); from the International Leafhopper Genome database for *Homalodisca vitripennis* (KK961671.1), at the National Agricultural Library, USDA, NAL, Beltsville, MD; and the International Psyllid genome open access database for *Diaphorina citri*, the Asian citrus psyllid at www.citrusgreening.org/organism/*Diaphorina_citri*/genome. A customized dsRNA construct was designed across a conserved area to target the full-length bantam microRNA and its precursor (Table 1) the template was ordered through GeneArt Gene Synthesis (Invitrogen, Pleasanton, CA).

T7 Template Synthesis

The bantam dsRNA construct was designed and synthesized with a 5' and 3' T7 promoter sequence (SEQ ID NO: 8) and used to generate T7 template for dsRNA synthesis. A conventional PCR reaction was performed to incorporate the T7 sequence using the Invitrogen Platinum® PCR SuperMix (Cat. No. 11306-016). Each reaction consisted of 100 ng purified RT template, 1.0 µL of 10 µM of forward and reverse T7 primers, and 45 µL Platinum® PCR SuperMix (Invitrogen). PCR was performed in an MJ Research Peltier Thermalcycler (PTC-200) using the following parameters: 3 min at 94° C., followed by 39 cycles of 15 s at 94° C., 30 s at 60°, and 30 s at 72° C., and a single final cycle of 72° C. for 10 min. The reaction was fractionated by electrophoresis for 45 min in a 2% agarose gel stained with ethidium bromide. All reactions generated an amplicon that was the appropriate product length. The bands were excised from the gel and purified using the Macherey-Nagel NucleoSpin® Gel and PCR Clean-up kit (REF 740609.250).

dsRNA Synthesis

Canonical bantam dsRNA was synthesized using the Ambion® MEGAscript® RNAi Kit (Ref. No. AM1626), and 2'-F cytosine and uracil modified non-canonical dsRNA was synthesized using the Lucigen® DuraScribe® T7 Transcription Kit (Cat. No. DS010925), per manual instructions.

*Spodoptera* Injection dsRNA Bioassay

A single concentration of dsRNA (8.5 µg) was diluted in 1% dimethyl sulfoxide (Cat. No. D5789, Sigma-Aldrich) to a final volume of 30 µL. Three larvae were injected with the non-canonical bantam dsRNA (SEQ ID NO:3 with all cytosines replaced with 2'-F-cytosine, and all uracils replaced with 2'-F-uracil) and three separate larvae were injected with the canonical bantam dsRNA (SEQ ID NO:3). Control larvae were injected with an identical concentration and volume of GFP dsRNA in 1% DMSO (diluted in water). Intrahaemocoelic injections were performed with a 30-gauge needle by inserting the needle between the fourth and fifth segment of the larvae and depositing the oligonucleotide at the side of the abdomen. *S. frugiperda* larvae were injected at $6^{th}$ instar to help alleviate injection induced mortality and to target bantam expression at the pupal stage. Larvae were returned to diet trays and allowed to feed to pupation.

*Spodoptera* Injection of ASO Bioassay

Two concentrations of ASO (SEQ ID NO: 1), 2 nmol and 4 nmol, were diluted in 1% dimethyl sulfoxide (Cat. No. D5789, Sigma-Aldrich) to a final volume of 30 µL. Six larvae were injected at each treatment concentration and control larvae were injected with an identical volume of 1% DMSO diluted in water. Intra-haemocoelic injections were performed with a 30-gauge needle, 1 mL sterile syringe, by inserting the needle between the fourth and fifth segment of the larvae and injecting the oligonucleotide near the wall inside of the abdomen. The *S. frugiperda* larvae were injected at $6^{th}$ instar to help alleviate injection induced mortality and to target bantam expression at the following pupal stage. Larvae were returned to diet trays and allowed to feed to pupation.

*Spodoptera* Feeding ASO Bioassay

In this assay, *Spodoptera* larvae fed on maize leaf pieces treated with dsRNA (SEQ ID NO: 3) or ASO, were analyzed for suppression of bantam in adult *S. frugiperda*, In each treatment 10 fourth instar larvae were fed the treatment by soaking 1 cm square pieces of maize leaf, Sweet corn (variety Early Golden Bantam) collected from week old seedlings, for 6 hours in 50 µL volumes of aqueous solutions of either 8 µg dsRNA for the unmodified canonical or modified noncanonical dsRNAs; or 4 nmol ASO solutions. Each larva consumed the entire leaf disc, within the 6 hr feeding access period, prior to being placed back onto normal rearing diet, each in one well of a multi-well plate. After 24 hours, a cohort of two larvae were collected for RNA extraction from each treatment group and each experiment trial. Larvae were first weighed and then placed in 2 mL microcentrifuge tubes with 1 mL Trizol reagent. Larvae were homogenized with a plastic pestle and stored at −80 C until RNA extraction. Larvae were kept on diet until they reach pupation. All larvae pupated on the same day, 6 days following leaf ingestion. Pupae were then placed in individual wells in a 12-well plate. The empty spaces between wells were filled with deionized water to maintain humidity levels. At 72 hours following pupation, a cohort of two pupae were collected from each treatment group and each experiment trial. Pupae were first weighed and then placed in 2 mL microcentrifuge tubes with 1 mL Trizol reagent, homogenized and stored at −80 C until RNA extractions.

Control-Reference Mass of *Spodoptera* Larvae

Developmental expression of bantam primarily in lepidopterans occurs during the pupal stage, thus, documentation of larval mass 24 hours post-ingestion served as the control-reference for future calculations of mass change of pupae. One would not expect to see a significant difference in mass at this time point given the period following ingestion. As hypothesized, there was no significant difference in mass between treatment groups.

Hemipteran Insect Feeding in-planta Citrus Cutting Assay. Citrus cuttings of new growth leaves and petiole, (approximately 2.5 cm in length were obtained and prepared using methods specified previously (Andrade & Hunter, Entomol. Exper. Applic., (2017) 162:389-96). Absorbed into each cutting was an aqueous solution that contained unmodified canonical dsRNA (SEQ ID NO:3), or modified noncanonical dsRNA (SEQ ID NO:3, with all cytosines and uracils modified as detailed above). The solution was nearly completely absorbed after 24 hrs, under laboratory conditions, fluorescent and LED lighting 18 hrs light: 6 hrs dark. Room temperature 22 C (+/−3 C). Five bioassay magenta box-cages per treatment were used. Cages were clear plastic, two-piece, 13 cm tall with fabric mesh screen top, circular openings 2.5 cm diameter, with nylon-screen. Replicates with 25 psyllid adults per cage were setup and given feeding access period of 12 days. Observations presented start at the 4$^{th}$ instar to adult emergence, examined pupae and adult stages for changes in morphology (wings, legs, darkened cuticle, etc . . . ) and increased mortality.

Whole plant, Soil Applied Treatment Feeding Assay

Solutions of 40 μg dsRNA (SEQ ID NO:3) in 10 mL water, of either dsRNA, unmodified canonical, or modified noncanonical (SEQ ID NO:3, with all cytosines and uracils modified as detailed above), or control water blank, or negative control dsRNA (Chinese Sacbrood Virus Capsid, dsRNA-CSBV [Genolutions, Inc]. Treatments were applied to the soil of small citrus seedlings (30 to 40 cm in height) in yellow plastic CONETAINERS, that were not previously watered for 4 days. Each treatment contained 3 seedling trees (Andrade, E. and Hunter, W. B. 2017). After 30 minutes, another 10 mL of water only was then applied to the soil of the citrus seedlings. Into each caged seedling 20 adult psyllids were released for 48 hrs days to oviposite eggs. Gender ratio was 1:1 female to male, providing an average of 25 eggs per tree. The adult insects were removed from the plants and the development of the psyllids monitored over a 10-day period. Data recorded numbers dead and changes in morphology, phenotypes (curled wings, legs, antennae, increased melanization, etc . . . ), at the pupae and adult stages.

Results

Bantam-ASO

Since bantam is largely implicated in developmental stages of growth, we hypothesized that duration of pupation may be affected in larvae treated with bantam-ASO (SEQ ID NO:1). On average, control adults emerged 14.2 days following pupation, whereas larvae treated with 2 nmol and 4 nmol bantam-ASO emerged at 13.8 and 13 days, respectively (FIG. 1). Given the variation in emergence, there was no statistical significance by standard deviation in the duration of pupation across control and treated larvae.

Despite this lack of effect on adult emergence, other phenotypic effects were observed—notably a significant decrease in adult weight. In this study, control adults had an average weight of 112.2 mg, whereas adults deriving from larvae treated with 2 nmol and 4 nmol bantam-ASO averaged weights of 100.6 and 100.5 mg, respectively (FIG. 2) Differences in mass were determined to be statistically significant when analyzed via one-way ANOVA ($p<0.0001$).

Figure 3:
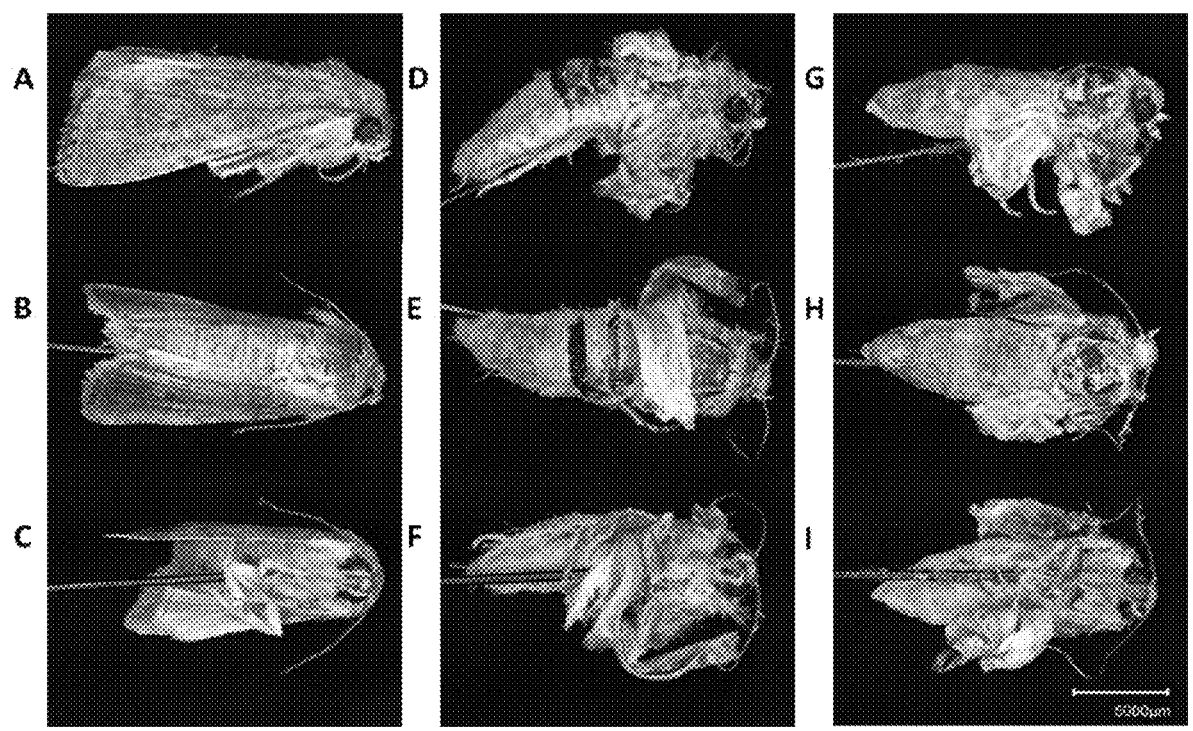
FIG. 3 provides pictorial data of the effects on wing formation in adult S. frugiperda treated with bantam-ASO (SEQ ID NO: 1). Control adults show no signs of curled or deformed wings (first column, A-C). Treated 4 nmol bantam-ASO adults show severe wing deformities and curling of the antennae (second column, D-F). Treated 2 nmol bantam-ASO adults displayed similar distorted wing and appendage phenotypes (third column, G-I).
Figure 4:
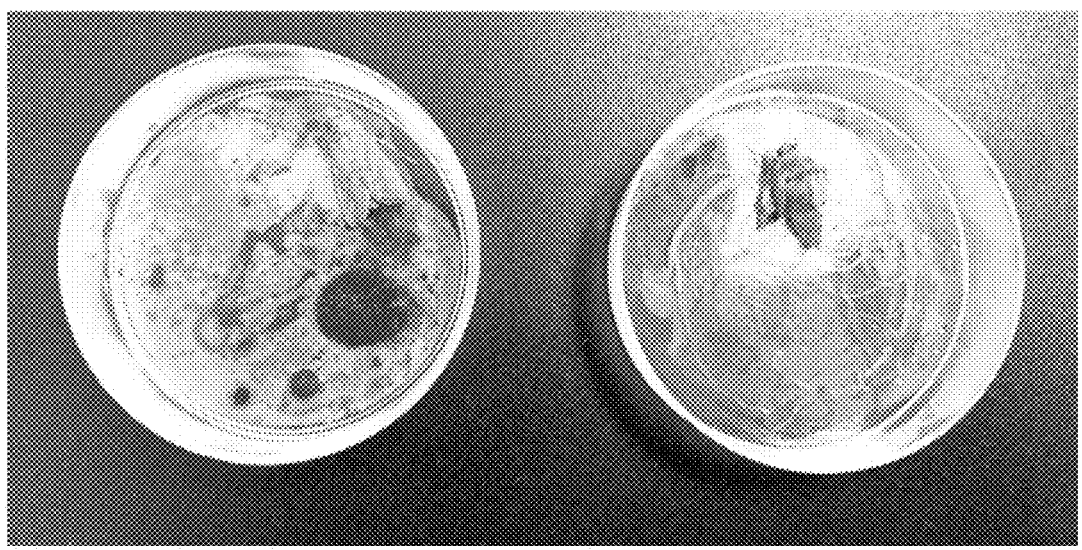
FIG. 4 provides pictorial data of the effects on frass production in adult S. frugiperda treated with bantam-ASO (SEQ ID NO: 1). Very little or no frass was observed from control adults following emergence (panel A). Treated adults, however, produced large quantities of watery, pink frass (panel B).
Figure 5:
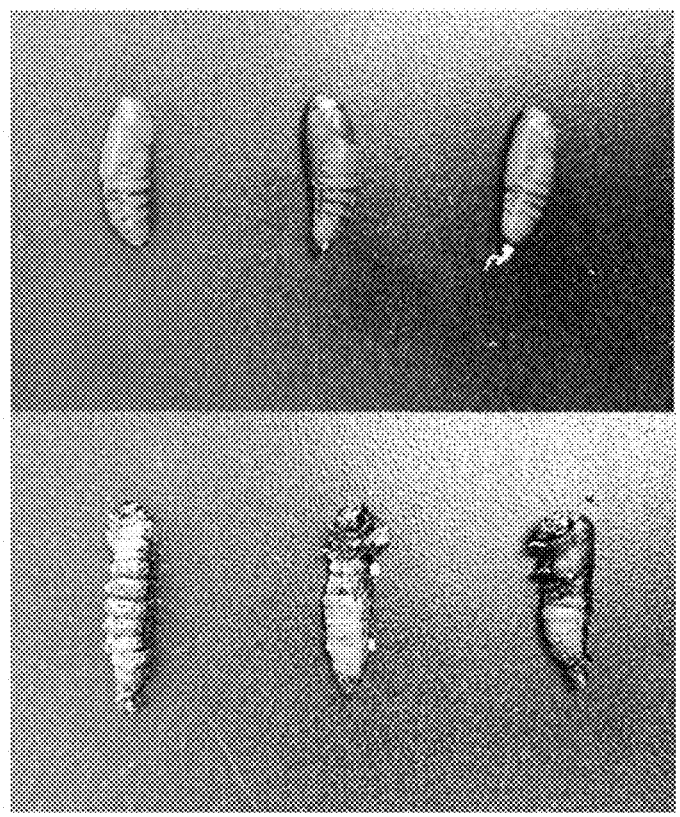
FIG. 5 provides pictorial data showing the effect of non-canonical bantam dsRNA (SEQ ID NO: 3) on pupae survival. All treated S. frugiperda pupae died (B). Mock treated Control larvae progressed through pupation with no observed deformities or mortalities (A). All control pupae emerged to adults.

Bantam-ASO caused wing deformities in adult *S. frugiperda*. Control adults show no signs of curled or deformed wings (FIG. 3, panels A-C). Treated 4 nmol bantam-ASO adults show severe wing deformities and curling of the antennae (FIG. 3, panels D-F), while the treated 2 nmol bantam-ASO adults treated with 2 nmol bantam-ASO displayed similar distorted wing and appendage phenotypes to those treated with 4 nmol (data not shown). The unmodified nucleotide canonical dsRNA treated larvae (G-I) had increased mortality, but some pupae eclosed to adults that had similar debilitating adult deformities of wings legs and antennae. All pupae receiving treatment with modified nucleotide noncanonical dsRNA pupae all died (FIG. 5, panel B.)

Canonical and Noncanonical Concatemers

Figure 6:
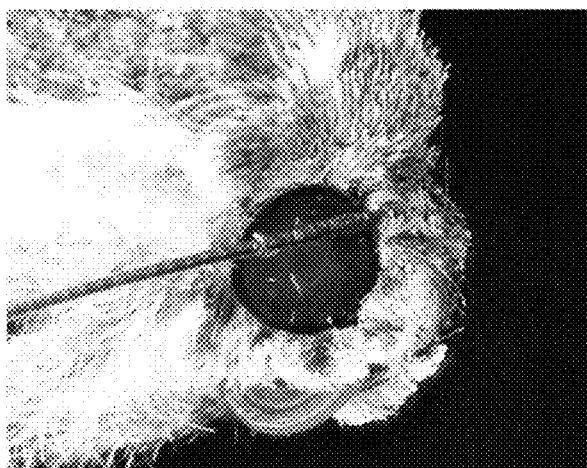
FIG. 6 provides pictorial data showing the effect of canonical bantam dsRNA (SEQ ID NO: 3) on eye color in S. frugiperda. Control adult (A) demonstrate typical eye color (dark brown), whereas canonical bantam dsRNA injected larvae resulted in an adult that emerged with a red eye color (B).
Figure 6:
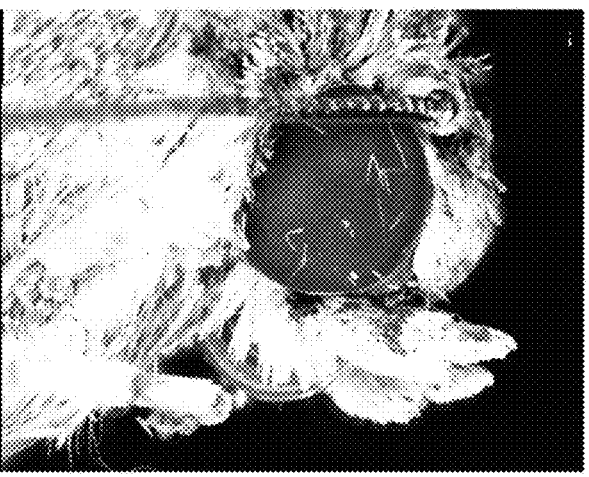

Larvae injected with the modified nucleotides non-canonical dsRNA construct (SEQ ID NO:3, with all cytosines and uracils modified as detailed above) began pupating 48 hr following injection. All three treated pupae (B), demonstrated incomplete pupation and died at this life cycle stage (FIG. 5, panel B). Larvae injected with the unmodified nucleotide canonical dsRNA construct (SEQ ID NO: 3) pupated and emerged as adults, with deformities in wings, and also had a red eye color phenotype (FIG. 6, panel B) not observed in mock treated controls (FIG. 6, panel A).

Figure 7:
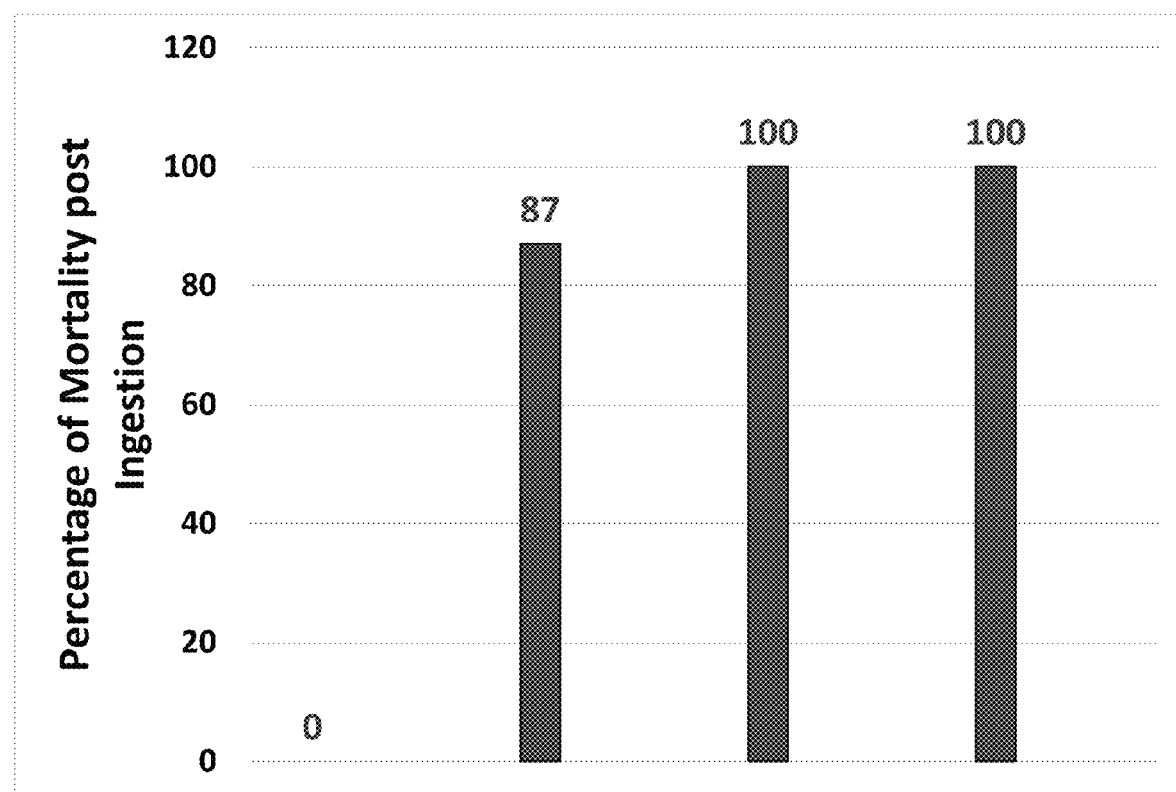
FIG. 7 provides graphical representation data showing the mortality effect of ASO (SEQ ID NO: 1—bar 2) or dsRNA (canonical SEQ ID NO: 3 (bar 3) and non-canonical SEQ ID NO:3 (bar 4)) ingested by S. frugiperda larvae on adults compared to control insects (bar 1).
Figure 8:
FIG. 8 provides pictorial data showing the effect of ingested unmodified nucleotide canonical dsRNA on psyllid adults. Caged citrus seedlings treated with dsRNA had previously had eggs deposited by adult psyllids. The psyllid nymphs developed while feeding on the treated seedlings, with increased mortality on treated citrus seeding trees. Adults that did eclose from treated nymphs had deformed wings, could not fly, and could not close their wings into the normal position (left panel), as compared to mock-treated controls (right panel). Additionally, adult emergence was significantly reduced in the treated group causing 40-60% increase in mortality. 100% of adults with deform phenotypes died within 4 days of eclosion.
Figure 8:
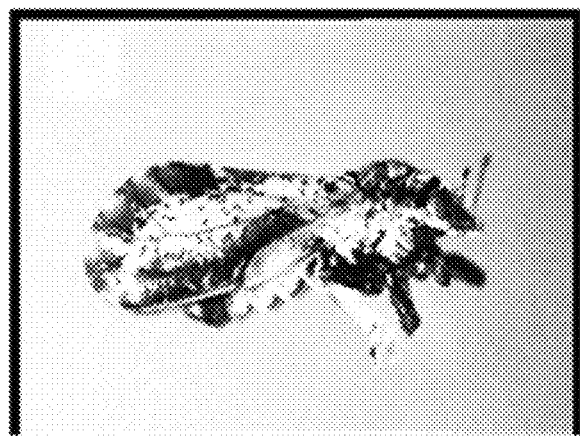
Figure 9:
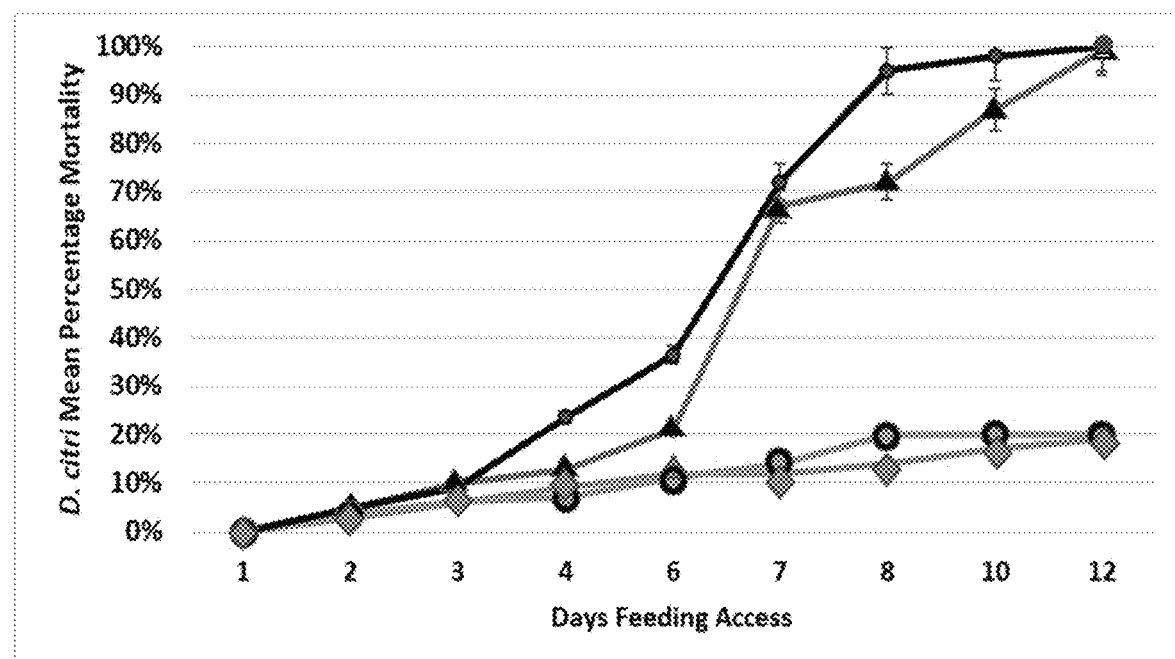
FIG. 9 provides graphical representation of data showing the effect of ingested unmodified nucleotide canonical dsRNA. Diamonds represent the water only control; open circles represent the non-relevant dsRNA control; filled circles represent canonical dsRNA; and triangles represent non-canonical dsRNA.

*Spodoptera* larvae fed on maize leaf pieces treated with dsRNA or ASO, were analyzed for suppression of bantam and mortality. Percentage mortality post ingestion by larvae is presented in FIG. 7. *Spodoptera* larvae fed on treated maize leaf tissue with unmodified canonical dsRNA (SEQ ID NO: 3) produced adults with 85% deformities, resulting in an average of 87% mortality post eclosion to adult. While larvae that fed on modified nucleotide noncanonical dsRNA (SEQ ID NO:3, with all cytosines and uracils modified as detailed above) treated maize tissue resulted in 100% deformities, and 100% mortality produced equally across the pupae and adult stages (50/50). *Spodoptera* larvae fed one treated maize leaf piece each, with 4 nmol bantam-ASO (2'-O-Me), resulted in 100% deformities, with 90% mortality at the pupae stage, with 100% mortality of adults that did eclose. All adults had severe wing deformities and curling of the antennae resulting in 100% mortality.

These results demonstrate the suppression of bantam produced significant mortality in larvae, pupae, and adults with wing deformity in emergent adults producing significant mortality (100%).

Figure 2:
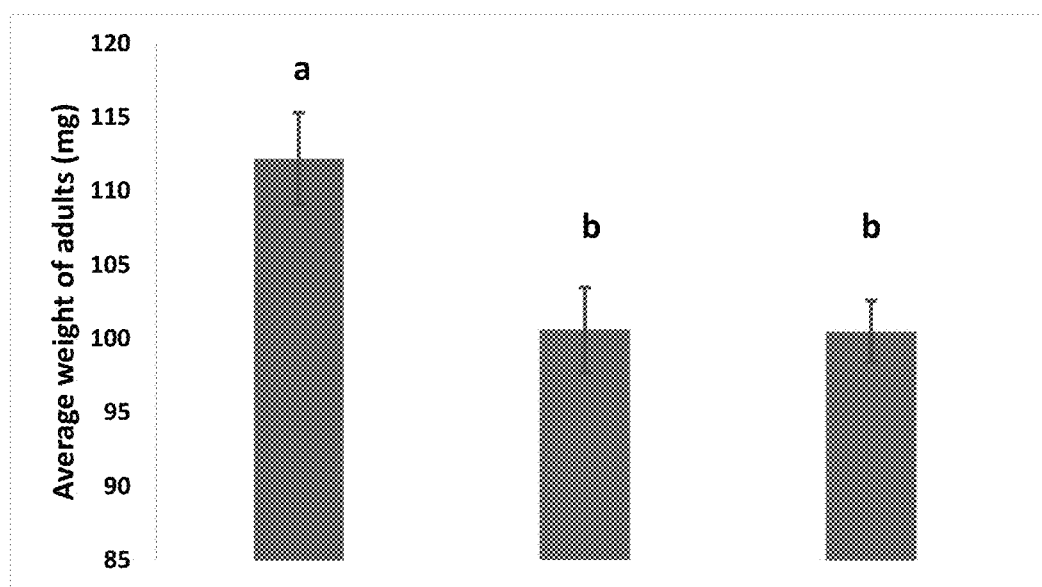
FIG. 2 provides graphic representation of data showing the effects on adult weight in *Spodoptera* treated with bantam-ASO (SEQ ID NO: 1). The first bar represents control adults, the second bar 2 nmol bantam-ASO, and the third bar 4 nmol bantam-ASO.

Despite this lack of effect on adult emergence, other phenotypic effects were observed—notably a decrease in adult weight. In this study, control adults had an average weight of 112.2 mg, whereas adults deriving from larvae treated with 2 nmol and 4 nmol bantam-ASO averaged weights of 100.6 and 100.5 mg, respectively (FIG. 2). Differences in mass were determined to be statistically significant when analyzed via one-way ANOVA ($p<0.0001$).

Canonical and Noncanonical Concatemers

Larvae injected with the non-canonical dsRNA construct (SEQ ID NO:3, with all cytosines and uracils modified as detailed above) began pupating 48 hr following injection. All three pupae tested demonstrated incomplete pupation and died at this life cycle stage (FIG. 5). Larvae injected with the canonical dsRNA construct (SEQ ID NO: 3) pupated an emerged as adults, but unexpectedly had a red eye coloration phenotype not observed in controls, or other *S. frugiperda* in our experiments (FIG. 6).

These results demonstrate the suppression of the miRNA bantam produced significant wing deformity in emergent adults, and caused significant mortality in larvae, preventing the emergence of adults (100%).

Example 2

Effects dsRNA-bantam on Hemipteran Insects Post-Ingestion

The dsRNA molecules utilized for these experiments were synthesized as mentioned above. Results from the feeding assay on treated citrus cuttings, presented changes in phenotype (curled wings in adults) and increased mortality (restricted molting success).

*D. citri*, were provided feeding access for 12 days to leaves absorbed with dsRNA-bantam, unmodified (SEQ ID NO: 3) and modified (non-canonical) oligonucleotide (SEQ ID NO:3, with all cytosines and uracils modified as detailed above), presented the greatest mortality of the population at the eclosion of the pupae. Increased pupae death resulted in decrease of adults. Deformed adults could not fly, and displayed some disruption of normal walking and feeding, resulting in 100% mortality (FIG. 8, left panel). The non-canonical dsRNA caused increased mortality earlier than the unmodified canonical dsRNA, but both produced 100% mortality by day 12 of the feeding access period. (FIG. 9)

Whole Plant, Soil Applied Treatment Feeding Assay

Results of the effects on developing psyllids, which average of 25 eggs per tree, three trees per treatment, that ingesting the dsRNA's over a 10-day feeding access on treated citrus trees, presented increased mortality during each molt. Response to 40 µg-dsRNA-bantam, canonical versus noncanonical when soil-applied to three citrus seedlings in containers per treatment. Noncanonical (SEQ ID NO:3, with all cytosines and uracils modified as detailed above) treatment produced 100% mortality 2 days before the canonical (SEQ ID NO: 3) treatment, showing a significant increase in RNAi activity. Both dsRNA treatments presented significantly greater mortalities, 100%, over the control water blank, or control dsRNA treatments which presented mortality rates of less than 12%.

While the invention has been described with reference to details of the illustrated embodiments, these details are not intended to limit the scope of the invention as defined in the appended claims.

The embodiment of the invention in which exclusive property or privilege is claimed is defined as follows:

1. A double-stranded ribonucleic acid (dsRNA) comprising a first strand comprising a sequence with at least 95% identity to any one of SEQ ID NO:5, SEQ ID NO: 6; or SEQ ID NO: 7 and a second strand complementary to the first strand.

2. The dsRNA of claim 1, wherein the first strand has at least 99% or 100% sequence identity to any one of SEQ ID NO:5, SEQ ID NO: 6; or SEQ ID NO: 7.

3. A double-stranded ribonucleic acid (dsRNA) comprising a first strand comprising SEQ ID NO:3 and a second strand complementary to the first strand.

4. A double-stranded ribonucleic acid (dsRNA) comprising a first strand comprising SEQ ID NO:4 and a second strand complementary to the first strand.

5. The dsRNA of claim 1, wherein the dsRNA is capable of inducing ribonucleic acid interference (RNAi) when ingested by a hemipteran or lepidopteran insect.

6. The dsRNA of claim 5, wherein the insect is S. frugiperda or D. citri.

7. The dsRNA of claim 1, wherein the dsRNA comprises at least one base comprising a 2'-O-methyl moiety.

8. The dsRNA of claim 1, wherein the dsRNA comprises at least one non-canonical nucleotide.

9. The dsRNA of claim 8, wherein the non-canonical nucleotide is 2'-fluorine-dCTP or 2'-fluorine-dUTP.

10. The dsRNA of claim 9, wherein each cytosine comprises 2'-fluorine-dCTP and each uracil comprises 2'-fluorine-dUTP.

11. A DNA molecule comprising a promoter functional in a host cell and a DNA encoding a dsRNA comprising a first strand and a second strand, wherein the first strand comprises a sense region with at least 95% sequence identity to any one of SEQ ID NO:5, SEQ ID NO: 6; or SEQ ID NO: 7 and a second strand complementary to the first strand.

12. A method of inducing RNAi in a hemipteran or lepidopteran insect, comprising contacting the dsRNA of claim 1 with a hemipteran or lepidopteran insect such that the insect ingests the dsRNA, thereby inducing RNAi in the insect.

13. The method of claim 12, wherein the insect is S. frugiperda or D. citri.

14. A method of inducing RNAi in a hemipteran or lepidopteran insect, comprising contacting a dsRNA with a hemipteran or lepidopteran insect such that the insect ingests the dsRNA, thereby inducing RNAi in the insect, wherein the first strand of the dsRNA comprises SEQ ID NO: 3, SEQ ID NO: 4, SEQ ID NO: 5, or SEQ ID NO: 6.

15. The method of claim 14, wherein the first strand of the dsRNA comprises SEQ ID NO: 4.

16. The method of claim 14, wherein the first strand of the dsRNA comprises SEQ ID NO: 5.

17. The method of claim 14, wherein the first strand of the dsRNA comprises SEQ ID NO: 6.

18. The method of claim 14, wherein the first strand of the dsRNA comprises SEQ ID NO: 3.

* * * * *